United States Patent
Omi et al.

(10) Patent No.: US 7,436,990 B2
(45) Date of Patent: Oct. 14, 2008

(54) BLOOD FLOW DYNAMIC ANALYZER AND ITS METHOD, AND IMAGE DIAGNOSTIC APPARATUS

(75) Inventors: Yasuo Omi, Nagareyama (JP); Osamu Miyazaki, Moriya (JP); Masahiko Aoyagi, Abiko (JP)

(73) Assignee: Hitachi Medical Corporation, Tokyo (JP)

( * ) Notice: Subject to any disclaimer, the term of this patent is extended or adjusted under 35 U.S.C. 154(b) by 613 days.

(21) Appl. No.: 10/527,226

(22) PCT Filed: Sep. 12, 2003

(86) PCT No.: PCT/JP03/11700

§ 371 (c)(1),
(2), (4) Date: Aug. 22, 2005

(87) PCT Pub. No.: WO2004/024001

PCT Pub. Date: Mar. 25, 2004

(65) Prior Publication Data

US 2006/0098852 A1    May 11, 2006

(30) Foreign Application Priority Data

Sep. 12, 2002   (JP)   ............................. 2002-266475

(51) Int. Cl.
*G06K 9/00* (2006.01)

(52) U.S. Cl. ......................... 382/128; 382/128; 382/173; 382/56; 382/154; 358/296; 358/135; 600/512; 395/101; 395/106; 395/114

(58) Field of Classification Search ................. 382/128, 382/173, 56, 154, 166; 395/101, 106, 114; 364/413.14; 378/901; 358/135, 296; 128/653.3, 128/661.08, 661.09; 600/512

See application file for complete search history.

(56) References Cited

U.S. PATENT DOCUMENTS

| 4,809,350 A | * | 2/1989 | Shimoni et al. ............. 382/238 |
| 4,862,359 A | * | 8/1989 | Trivedi et al. ............... 600/544 |
| 5,530,789 A | * | 6/1996 | Miyazaki ..................... 358/1.1 |
| 6,389,304 B1 | * | 5/2002 | Van Den Brink et al. .... 600/419 |

(Continued)

OTHER PUBLICATIONS

Three-Dimensional Blind Deconvolution of SPECT Images; Max Mignotte and Jean Meunier, IEEE 2000.*

Leif Østergaard et al. (1996) "High Resolution Measurement of Cerebral Blood Flow Using Intravascular Tracer Bolus Passages. Part I: Mathematical Approach and Statistical Analysis", High Resolution CBF Measurement I: pp. 715-725.

*Primary Examiner*—Andrew W. Johns
*Assistant Examiner*—Nancy Bitar
(74) *Attorney, Agent, or Firm*—Cooper & Dunham LLP

(57) ABSTRACT

According to the present invention, a Fourier transformation is executed on a time-concentration curve for an inflow artery and a time-concentration curve for each tissue on the basis of a dynamically acquired tomogram. An inverse filter is then calculated from the Fourier-transformed time-concentration curve for the inflow artery. The Fourier-transformed time-concentration curve for each tissue is multiplied by the inverse filter to generate a transfer function for the tissue. The thus generated transfer function for each tissue is used to calculate biological function information. Thus, if biological function information on an organ to be analyzed is to be obtained from a tomogram provided by a computer tomograph, very quantitative biological function information can be obtained at a low contrast rate. In particular, it takes only a minimum calculation time to obtain biological function information.

30 Claims, 11 Drawing Sheets

U.S. PATENT DOCUMENTS 6,546,275 B2 * 4/2003 Carroll ..................... 600/419
6,618,609 B2 * 9/2003 Liu et al. .................. 600/419
2006/0215889 A1 * 9/2006 Omi et al. ................. 382/128
2008/0015440 A1 * 1/2008 Shandas et al. ............ 600/458

* cited by examiner

Fig. 4(a)
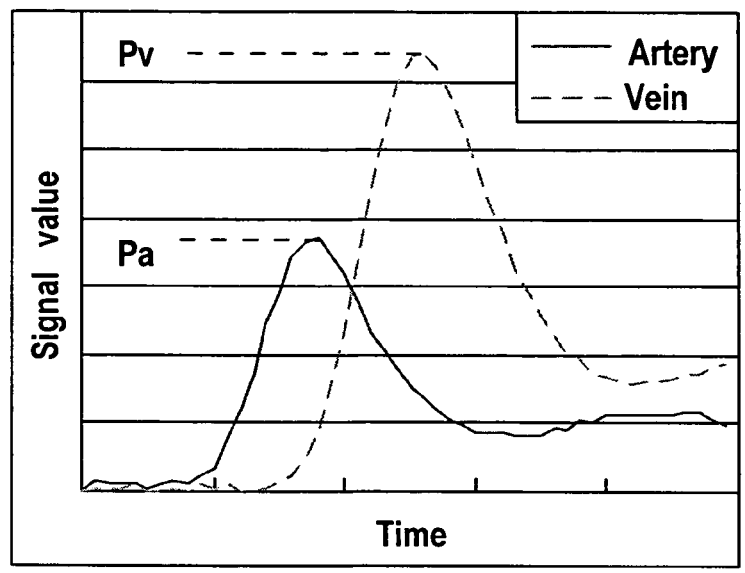
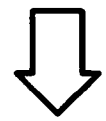
Fig. 4(b)
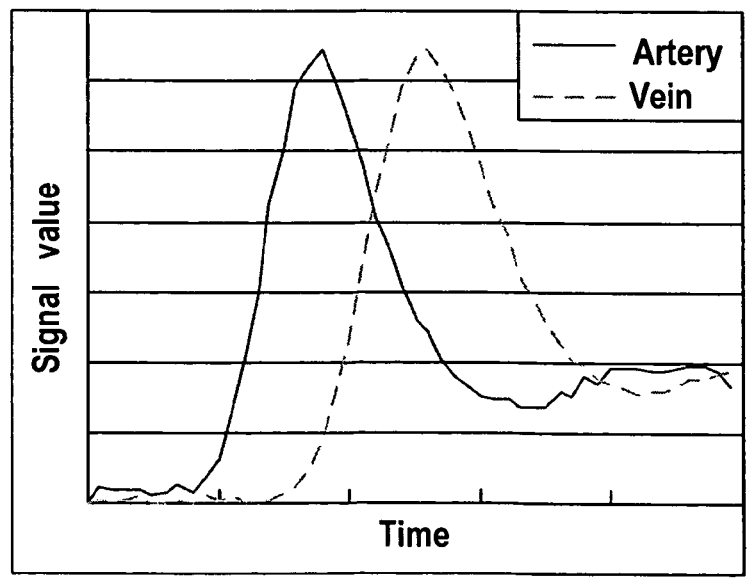

Fig. 5(a)
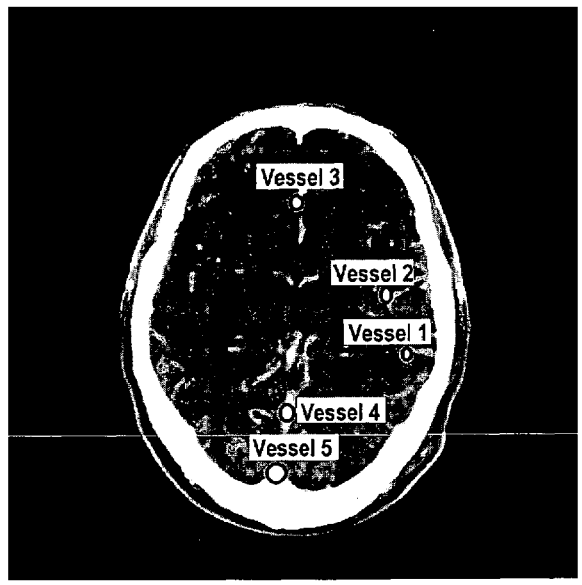
Fig. 5(b)
|  | Vessel diameter | Peak value |
|---|---|---|
| Vessel 1 | R1 | P1 |
| Vessel 2 | R2 | P2 |
| Vessel 3 | R3 | P3 |
| Vessel 4 | R4 | Pth |
| Vessel 5 | R5 | Pth |
Fig. 5(c)
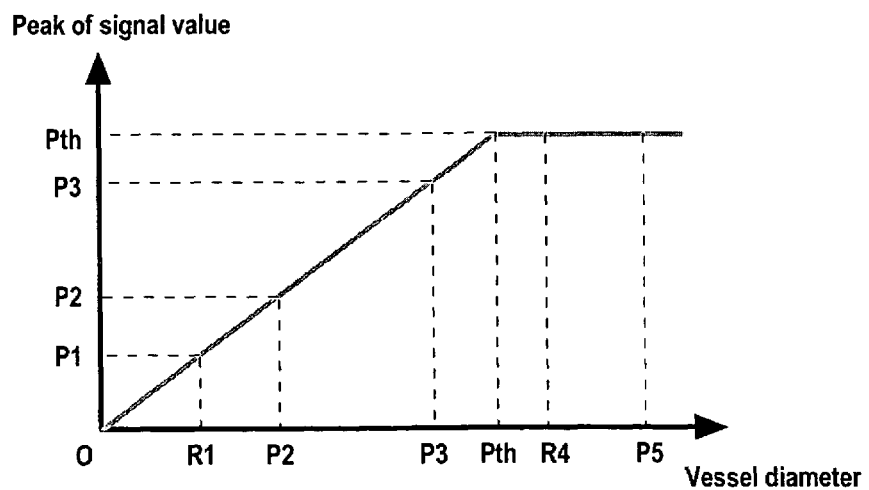

Target tissue

BLOOD FLOW DYNAMIC ANALYZER AND ITS METHOD, AND IMAGE DIAGNOSTIC APPARATUS

TECHNICAL FIELD

The present invention relates to a blood flow dynamic analyzing apparatus and method and an image diagnosing apparatus, and in particular, to a technique that is useful for using a blood flow dynamic analyzing apparatus or the like to execute image analysis on a tomogram provided by a computer tomogram diagnosing apparatus that can use an X ray or an electromagnetic wave to provide biological function information dependent on a temporal variation in a subject.

BACKGROUND ART

A conventional blood flow dynamic analyzing apparatus uses, for example, an X-ray CT apparatus to carry out dynamic imaging. During the imaging, an iodine-based contrast medium is injected into a patient. The blood flow dynamic analyzing apparatus thus provides information on a temporal variation in the concentration of the injected contrast medium. A time-concentration curve can be obtained from the temporal variation. Then, by analyzing the curve of the time-concentration curve, it is possible to obtain biological function information such as blood flow dynamics. Typical algorithms for analyzing the blood flow dynamics include a first moment method (gamma-fitting method), a maximum slope method, and a deconvolution method.

First, the first moment method (gamma-fitting method) uses a gamma function to approximate the time-concentration curve. Then, blood flow information is calculated from a peak value of the approximate curve and an area under the curve. Next, the maximum slope method calculates a blood flow by dividing the maximum value of slope of the time-concentration curve for each tissue by the maximum value of a rise in a CT value in an arterial input function.

However, the first moment method (gamma-fitting method) and the maximum slope method require that about 8 to 10 ml/sec of contrast medium be injected into the subject. Disadvantageously, this is a heavy burden on the physical strength of the subject into which the contrast medium is injected. Moreover, disadvantageously, the gamma fitting method enables qualitative evaluation but not quantitative evaluation.

Thus, efforts were made to develop a blood flow analyzing method which can reduce the contrast rate and which enables quantitative evaluation. As a result, the deconvolution method has been proposed (see the well-known document shown below). The deconvolution method subjects an arterial input function and a tissue output function to deconvolution to generate an impulse residue function. Then, blood flow information is calculated from a peak value or an area under the curve of the impulse residue function generated. The deconvolution method advantageously enables examinations at a low contrast rate of about 3 to 5 ml/sec. Accordingly, the deconvolution method requires a contrast medium injection speed that is only about half that of the first moment method (gamma-fitting method) or the maximum slope method.

(Well-known document: L. Ostergarrd etc.: High Resolution Measurement of Cerebral Blood Flow using Intravascular Tracer Bolus Passages: 1996; Magnetic Resonance in Medicine Vol. 36: P. 715-725)

However, the deconvolution method requires a plurality of integrations in the data conversion calculation that determines the impulse residue function from the arterial input function and tissue output function. Consequently, the deconvolution method requires a time for the calculation.

It is an object of the present invention to enable blood flow dynamic analysis to be carried out in a short time.

DISCLOSURE OF THE INVENTION

To accomplish the above object, the present invention is characterized by inputting a tomogram acquired by a tomograph, determining a time-concentration curve indicative of information on a temporal variation in each pixel of the input tomogram, determining a time-concentration curve for an inflow artery from the determined time-concentration curve for each pixel of the tomogram, generating an inverse filtering function from the determined time-concentration curve for the inflow artery, generating a transfer function for each pixel of the tomogram on the basis of the reverse function generated and the time-concentration curve for each pixel of the tomogram, using the generated transfer function for each pixel of the tomogram to determine a blood flow dynamic analysis image.

This makes it possible to, for example, generate a transfer function for each tissue by multiplying, on a frequency space, the inverse filter of the time-concentration curve for the inflow artery and a time-concentration curve for the tissue. It is thus possible to reduce the time for calculations compared to the conventional deconvolution method.

Further, according to a desirable embodiment, the present invention is characterized by extracting a maximum connected pixel area from the tomogram, creating a mask image showing the extracted maximum connected pixel area, and using the mask image created to remove unwanted areas from the input tomogram which are different from the area of the mask image and which include room air, a bed, and bones.

Thus, the areas unnecessary for the blood flow analysis are removed to reduce the amount of data to be analyzed. This makes it possible to reduce the time required by the above biological function information calculating means or the like to execute calculations.

Furthermore, according to another desirable embodiment, the present invention is characterized by determining a time-concentration curve for an outflow vein from the determined time-concentration curve for each pixel of the tomogram and finding peak values of the time-concentration curve for the inflow artery and the time-concentration curve for the outflow vein, and by correction of a partial volume averaging (simply referred to as "PVA" below) effect in the time-concentration curve for the inflow artery such that the peak value of the time-concentration curve for the inflow artery matches the peak value of the time-concentration curve for the outflow vein.

Specifically, if an X-ray CT apparatus is used to examine blood flow dynamics, the PVA effect reduces the CT value of a voxel containing the artery compared to its inherent value. This degrades the quantitativeness of the results of the analysis. Therefore, correction of the PVA effect enables a clear blood flow dynamic analysis.

BRIEF DESCRIPTION OF THE DRAWINGS

FIGS. 4(a) and 4(b) are diagrams showing a method for correcting the PVA effect according to the present embodiment;

FIGS. 5(a) to 5(c) are diagrams showing another method for correcting the PVA effect according to the present embodiment;

BEST MODE FOR CARRYING OUT THE INVENTION

With reference to the accompanying drawings, a detailed description will be given of a preferred embodiment of a blood flow dynamic analyzing apparatus according to the present invention.

Figure 1:
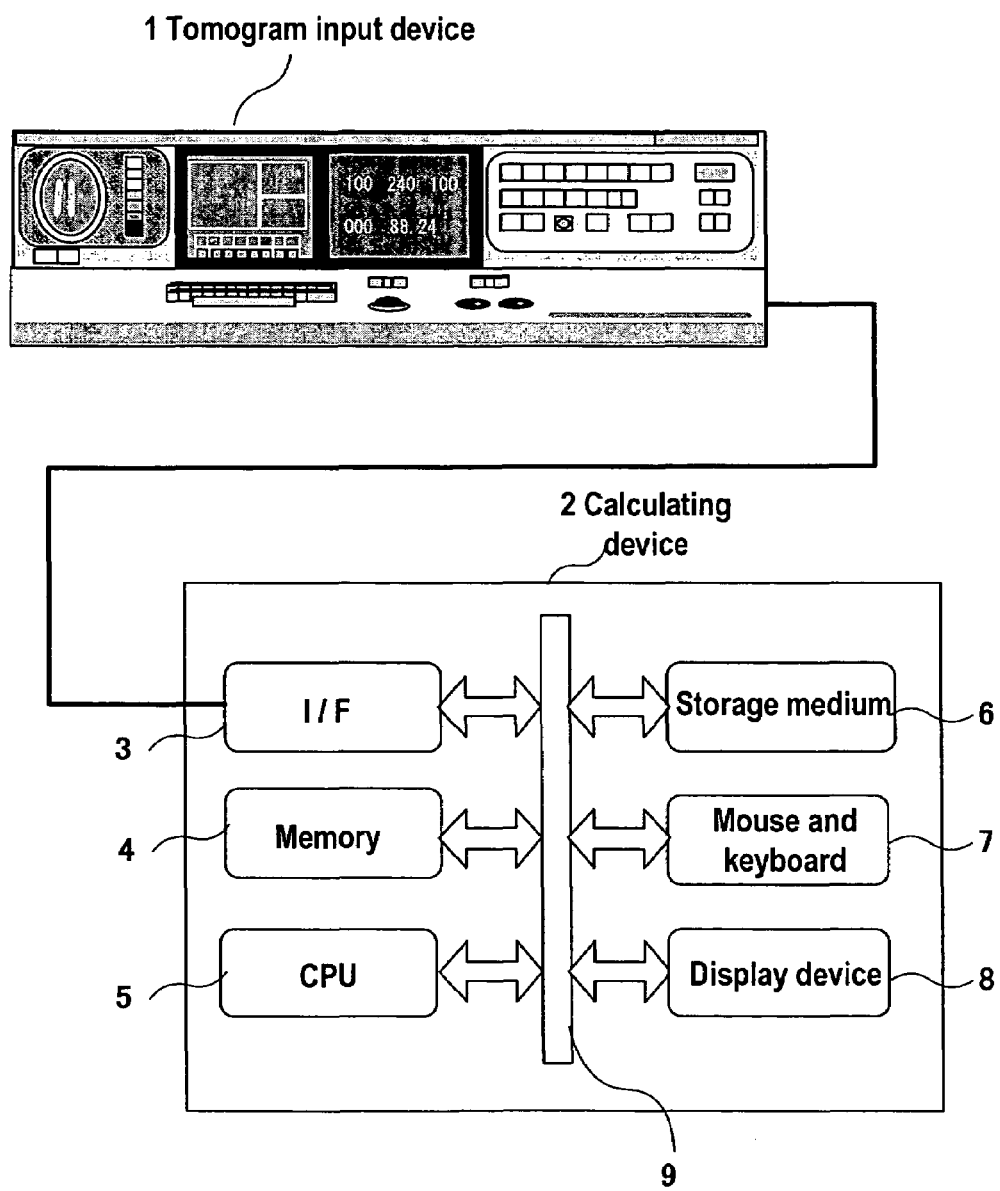
FIG. 1 is a block diagram showing an example of the hardware configuration of a blood flow dynamic analyzing apparatus according to the present invention.

FIG. 1 is a block diagram showing an example of the hardware configuration of a blood flow dynamic analyzing apparatus according to the present invention. As shown in the FIG. 1, the blood flow dynamic analyzing apparatus is composed of a tomogram input device 1 to which a tomogram acquired mostly by a computer tomography imaging apparatus is input and a calculating device 2 that executes various calculations such as image analysis.

The tomogram input device 1 and the calculating device 2 need not necessarily be separate from each other but may be integrated.

The calculating device 2 is composed of an interface (I/F) 3 that loads a tomogram from the tomogram input device 1, a memory 4 in which tomograms and results of calculations are temporarily stored, a central processing unit (CPU) 5 that executes various calculations, a recording medium 6 such as a hard disk on which results of calculations and function images are recorded, an external input device 7 such as a mouse or a keyboard, and a display device 8 that displays results of processing. These components are connected together by a common bus 9.

Figure 2:
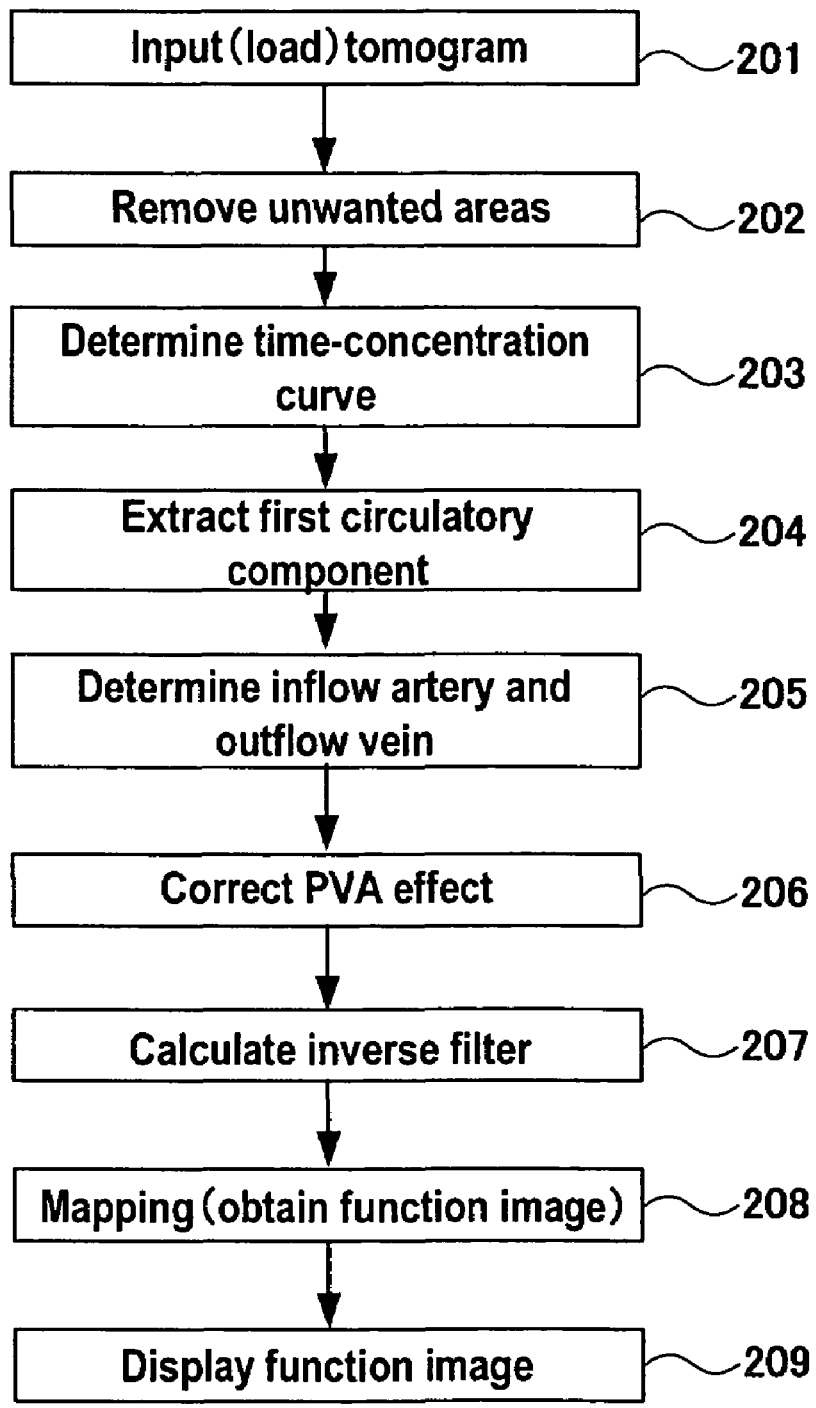
FIG. 2 is a flowchart showing a procedure from inputting of a tomogram to the blood flow dynamic analyzing apparatus according to the present invention to displaying of a function image carried out by the blood flow dynamic analyzing apparatus.

FIG. 2 is a flowchart showing a procedure from inputting of a tomogram to the blood flow dynamic analyzing apparatus according to the present invention to displaying of a function image carried out by the blood flow dynamic analyzing apparatus.

First, the tomogram input device 1 selects a tomogram of a subject on which a blood flow dynamic analysis is to be executed. The tomogram input device 1 then inputs the selected tomogram to the calculating device 2 (step 201). The input tomogram is temporarily stored in the memory 4 or saved to the recording medium 6. If the tomogram input device 1 and the calculating device 2 are integrated, the external input device 7 selects a tomogram of a subject on which a blood flow dynamic analysis is to be executed. The selected tomogram is read from the recording medium 6 and temporarily stored in the memory 4.

Subsequently, the CPU 5 removes areas in the tomogram which show room air, a bed, bones, and the like and which are unnecessary for analyzing biological function information (step 202). A method for removing unwanted areas will be described later.

Then, the CPU 5 obtains a time-concentration curve indicative of information on a temporal variation, from the tomogram for each pixel (step 203). Subsequently, the CPU 5 obtains a first circulatory component from the time-concentration curve (step 204). To obtain the first circulatory component, it is possible to use an arbitrary well-known algorithm such as gamma function fitting or extrapolation based on an exponential function.

Subsequently, the CPU 5 determines an artery used for an artery input function (referred to as an inflow artery below) and a vein used for quantization such as correction of the PVA effect (referred to as an outflow vein) (step 205). An operator may manually specify an inflow artery and an outflow vein while viewing a tomogram. It is also possible to automatically determine an inflow artery and an outflow vein for an organ to be analyzed on the basis of a peak value and peak time of a time-concentration curve.

Before the inflow artery and the outflow vein are automatically determined, central pixels of the inflow artery and outflow vein are first calculated. In order to automatically select the central pixels of the inflow artery and outflow vein, it is possible to utilize a difference between the maximum and minimum values of a time-concentration curve for each tissue (referred to as $\Delta TDC$ below) or a difference in peak time or peak value characteristic. For example, by selecting one pixel having a peak value equal to or larger than a predetermined threshold and having the earliest peak time from pixels having a $\Delta TDC$ equal to or larger than a certain threshold, it is possible to automatically select the central pixel of the inflow artery. Further, the central pixel of the outflow vein can be automatically selected by selecting one of pixels having a $\Delta TDC$ equal to or larger than a certain threshold, the one having a peak value equal to or larger than a predetermined threshold and having the latest peak time. Then, for pixels around the central pixels of the inflow artery and outflow vein, pixels having a peak value equal to or larger than the threshold are separated from those having a peak value smaller than the threshold. Then, connected pixels including the central pixels are extracted from the pixels having a peak value equal to or larger than the threshold. As a result, an inflow artery area and an outflow vein area are determined. The central pixels alone may be determined to be an inflow artery and an outflow vein.

Then, the CPU 5 corrects the PVA effect (step 206). A method for correcting the PVA effect will be described later. Subsequently, the CPU 5 executes an inverse filter calculation on each pixel to calculate biological function information (step 207). The reverse filter calculation will be described later.

A function image is obtained by mapping biological function information analyzed for each pixel (step 208). The display device then displays the function image (step 209). Step 204 may be executed between steps 206 and 207.

Now, a method for removing unwanted areas will be described.

Figure 3:
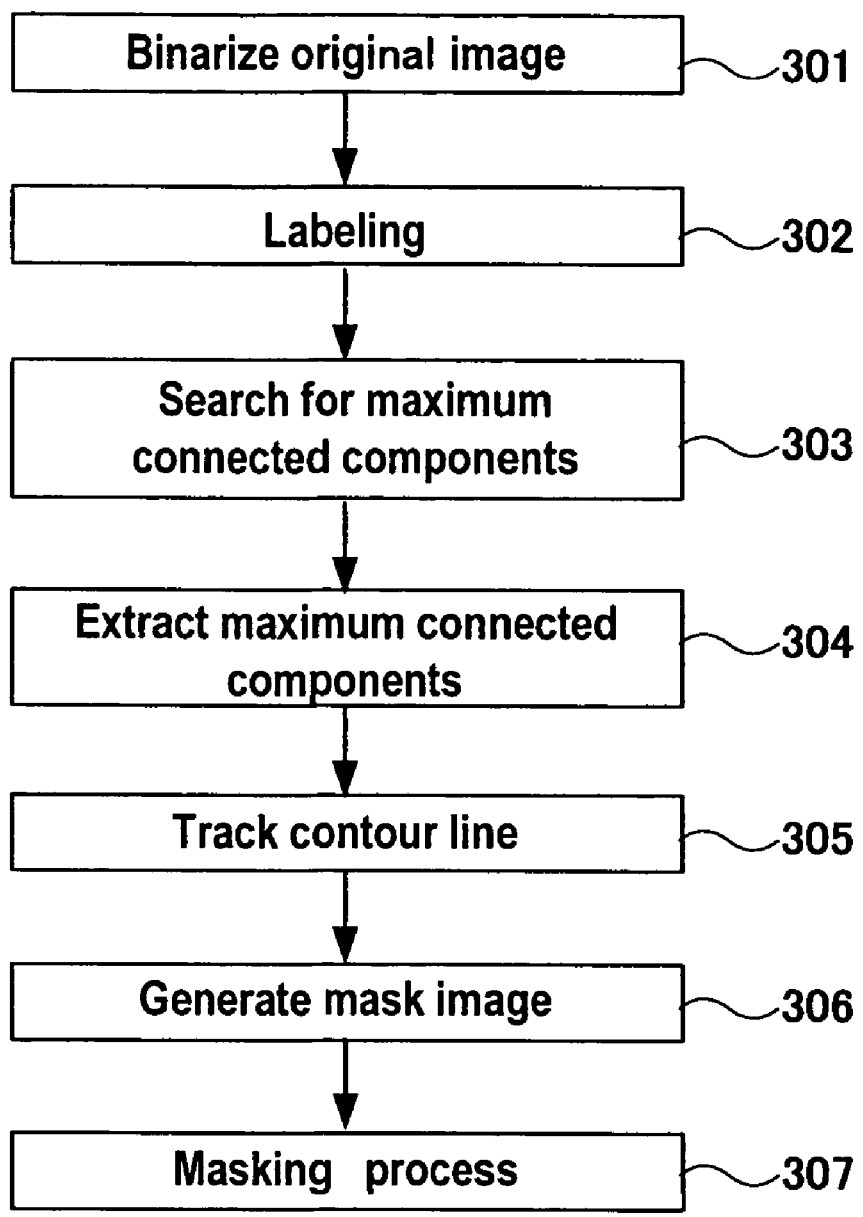
FIG. 3 is a flowchart showing a method for removing unwanted areas.

FIG. 3 is a flowchart showing a method for removing unwanted areas. As shown in the FIG. 3, the CPU 5 first binarizes the tomogram input in step 201 in FIG. 2 (step 301). The binarizing process is executed by, for example, replacing, in a tomogram, pixels having a value equal to or larger than the threshold with 1, while replacing pixels having a value smaller than the threshold with 0. The threshold may be such an arbitrary value as enables a living tissue to be analyzed to be separated from room air. For example, if the input tomogram is a CT image, the threshold may be set at about −200.

Subsequently, the CPU 5 labels the image binarized in step 301 (step 302). The labeling process is executed by applying the same number (label) to all the connected pixels (connected components), while applying a different number to different connected components. If adjacent pixels both have a value of 1, they are connected together. Values applied as labels are, for example, consecutive numbers starting at 50.

Then, the CPU 5 searches for the maximum connected components (step 303). Searching the maximum connected components is executed by scanning the entire labeled image, counting the number of pixels for each label value, and selecting connected components having a label value indicating the largest number of pixels. Subsequently, the CPU 5 extracts the maximum connected components (step 304). The maximum connected components are extracted by replacing, with 0, all the pixels except those selected in step 303 and having a label value indicative of the largest number of pixels. Thus, in the binarizing stage, pixel values for unwanted areas such as the bed and an intravenous drip infusion tube which may have their pixel values replaced with 1 are replaced with 0.

Then, the CPU 5 tracks the contour of the maximum connected components to extract the contour line of the outermost periphery of the maximum connected components (step 305). The contour line is tracked by horizontally scanning the image in which only the maximum connected components are left in step 304, starting with a pixel in an upper left corner of the image, using a pixel encountered first and having a nonzero label value as a start point to track the contour counterclockwise, and ending the tracking when the scan returns to the start point. A value different from the label value, for example, 1, is substituted for the pixels on the contour line.

Subsequently, the CPU 5 fills 1 into the inside of the contour line determined in step 305 to create a mask image (step 306). To fill the inside of the contour line with 1, it is possible to apply a seed fill algorithm that is a conventionally known process of filling the interior of a closed area with data using one point inside the closed area as a start point. In the present embodiment, the closed area is the contour line determined in step 305. Further, points inside the closed area are pixels with the label value for the maximum connected components determined in step 304. The inside of the contour line can be filled with data by detecting one pixel with this label value and using it as a start point to execute a seed fill process.

Then, the CPU 5 multiplies the input image (tomogram) by the mask image created in step S306 to remove pixels located outside the mask area (step 307). Specifically, each pixel of the mask image is examined. When a zero pixel is detected, the minimum luminance is substituted for a pixel in the original image corresponding to the coordinates of the zero pixel. This operation is performed on all the pixels to remove the pixels located outside the mask area from the input image.

Now, a method for correcting the PVA effect will be described.

FIG. 4 is a diagram showing a method for correcting the PVA effect according to the present embodiment. For example, in case that biological function information on the brain is analyzed, in general, the anterior or middle cerebral artery is used as an inflow artery, and the superior sagittal venous sinus is used as an outflow vein. According to the study of Lapin et al. (Journal of Computer Assisted Tomography 1993; Vol. 17: P. 108-114), the PVA effect reduces the signal value of a voxel containing an artery, so that a time-concentration curve for the anterior or middle cerebral artery, which are an inflow arteries, has a value smaller than an inherent one. Further, according to the study of Lee et al. (American Journal of Neuroradiology 1999; Vol. 20: P. 63-73), a vessel of diameter at least 1.73 mm is not affected by the PVA effect, so that a time-concentration curve for the superior sagittal venous sinus, which is outflow vein, is not affected by the PVA effect.

Accordingly, the time-concentration curves for the inflow artery and outflow vein are generally as shown in FIG. 4($a$). A peak value Pa of the time-concentration curve for the inflow artery is smaller than that Pv for the time-concentration curve for the outflow vein by a value corresponding to a decrease in signal value attributed to the PVA effect. Ideally, the concentration of a contrast medium in the vessel is constant regardless of its diameter. Consequently, in case of no influence of the PVA effect, the peak signal value is constant regardless of the vessel diameter.

Therefore, when the peak value for the inflow artery is defined as Pa and the peak value for the outflow vein is defined as Pv, the PVA effect on the inflow artery can be corrected by multiplying the time-concentration curve for the inflow artery by Pv/Pa as shown in FIG. 4($b$). When a time-concentration curve for the inflow artery observed at a time t before the correction of the PVA effect is defined as AIFpva(t) and a time-concentration curve for the inflow artery observed at a time t after the correction of the PVA effect is defined as AIF(t), the correction may be made so that the formula shown below is established between these time-concentration curves.

$$AIF(t) = AIFpva(t)\frac{Pv}{Pa} \tag{1}$$

FIG. 5 is a diagram showing another method for correcting the PVA effect according to the present embodiment.

If there is any past clinical image taken under the same imaging and contrast conditions as those for examinations to be carried out, the image can be used to correct the PVA effect.

For example, in the clinical image shown in FIG. 5($a$), for a plurality of vessels 1 to 5 contained in the tomogram, vessel diameters R1 to R5 and peak values of time-concentration curves for the vessels are calculated. These values are shown in FIG. 5($b$). When these values are plotted in a graph, such a curve as shown in FIG. 5($c$) is obtained. Description will be given later of a method for calculating the vessel diameter and the peak value. The thinner the vessel diameter is, the more pronounced the PVA effect is. The vessel is not subjected to the PVA effect when its diameter has at least a certain value. Accordingly, the curve in FIG. 5($c$) rises gradually until a diameter Rth is reached. Then, the peak value becomes flat for R equal to or larger than Rth. In this flat state, the peak value is defined as Pth for convenience. The vessel diameter of the inflow artery is defined as Ra. The peak value of the time-concentration curve for the inflow artery is defined as Pa.

If Ra is smaller than Rth, the PVA effect on the inflow artery can be corrected by multiplying the time-concentration curve for the inflow artery by Pth/Pa. When a time-concentration curve for the inflow artery observed at a time t before the correction of the PVA effect is defined as AIFpva(t) and a time-concentration curve for the inflow artery observed at a time t after the correction of the PVA effect is defined as AIF(t), the correction may be made so that the formula shown below is established between these time-concentration curves.

$$AIF(t) = AIFpva(t)\frac{Pth}{Pa} \tag{2}$$

Now, description will be given of a method for calculating the vessel diameter and the peak value.

Figure 6:
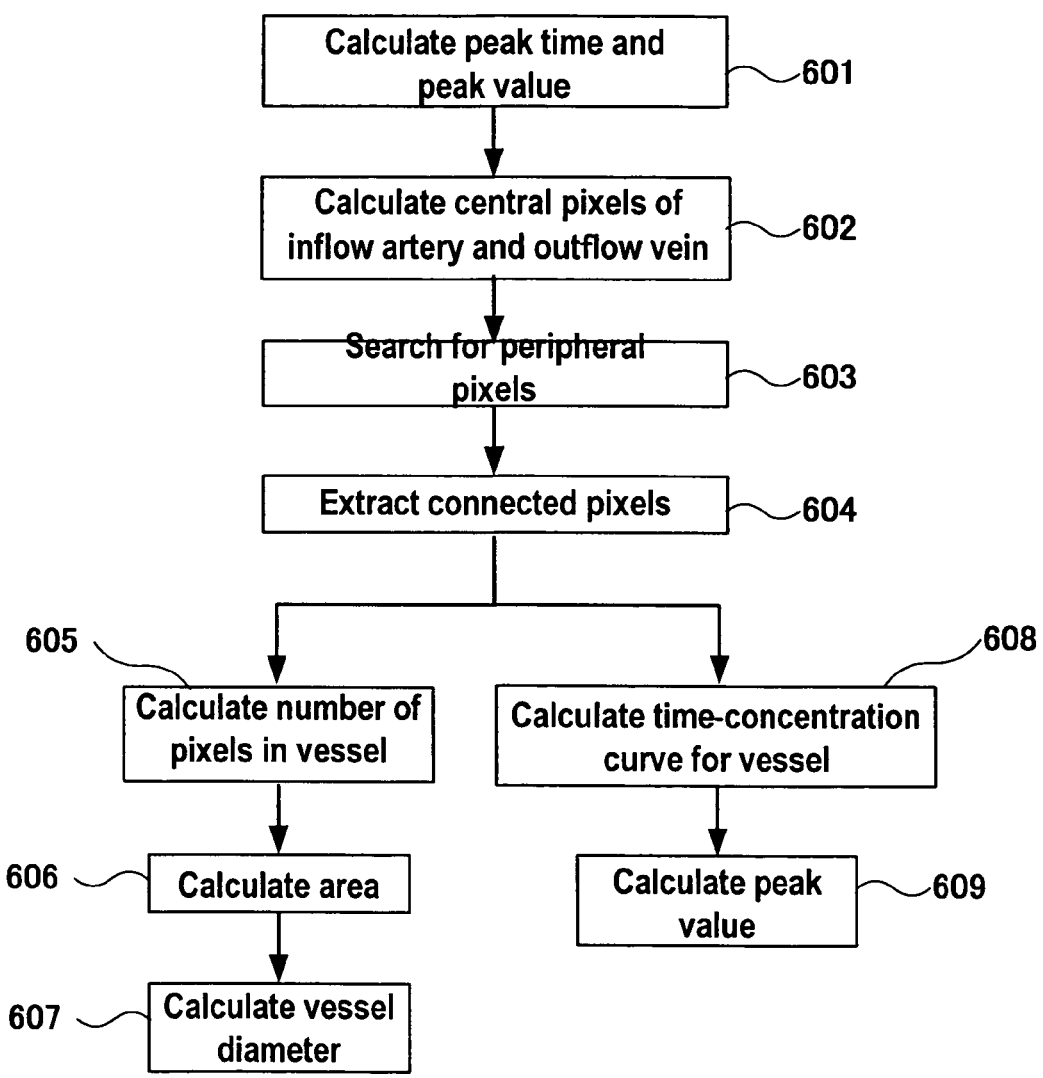
FIG. 6 is a flowchart showing a procedure for calculating a vessel diameter and a peak value according to the present embodiment.

FIG. 6 is a flowchart showing a procedure for calculating the vessel diameter and the peak value according to the present embodiment. First, the CPU 5 calculates the peak time and peak value of each time-concentration curve (step 601). Then, the CPU 5 calculates the central pixel of the vessel (step 602). The characteristics of the peak value may be utilized to calculate the central pixel. Selection of a pixel with the largest peak value enables the automatic selection of the central pixel of the vessel. Subsequently, for pixels located around the central pixel of the vessel, the CPU 5 separates pixels having a peak value equal to or larger than a threshold from pixels having a peak value smaller than the threshold (step 603). Subsequently, the CPU 5 extracts connected pixels including the central pixel from the pixels determined in step 603 to have a peak value equal to or larger than the threshold. Thus, a vessel area is determined (step 604).

Then, the CPU 5 calculates the number of pixels in the vessel area (step 605). The CPU 5 then calculates the size of the vessel area from the calculated number of pixels (step 606). Since the area of one pixel has a fixed value in every apparatus, the size S of the vessel area is obtained by multiplying the area of one pixel by the number of pixels determined in step 605.

Subsequently, the CPU 5 calculates the vessel diameter R (step 607). The shape of the vessel on the tomogram may approximated by a circle. Accordingly, the formula shown below holds true for the vessel diameter R and area S. The vessel diameter may be calculated in accordance with the formula.

$$R = \sqrt{\left(\frac{S}{\pi}\right)} \tag{3}$$

Then, the CPU 5 calculates a time-concentration curve for the vessel (step 608). Since the time-concentration curve for each pixel was calculated in step 203, the time-concentration curve for the vessel is obtained by calculating the average of the time-concentration curves for all the pixels in the vessel area. Instead of taking the average, it is possible to carry out arbitrary weighting in accordance with the distance from the central pixel of the vessel calculated in step 602.

Then, the CPU 5 calculates the peak value of the time-concentration curve for the vessel (step 609). It is possible to reverse the order of the processing from step 605 to step 607 and the processing from step 608 to step 609. In the present embodiment, the vessel is extracted utilizing the characteristics of the peak value. However, the method for extracting the vessel is not limited to this. An arbitrary method may be used provided that it can accurately extract the vessel. Alternatively, the vessel may be extracted by manually specifying the vessel area while viewing the tomogram.

Now, the concept of an inverse filter method will be described.

Figure 7:
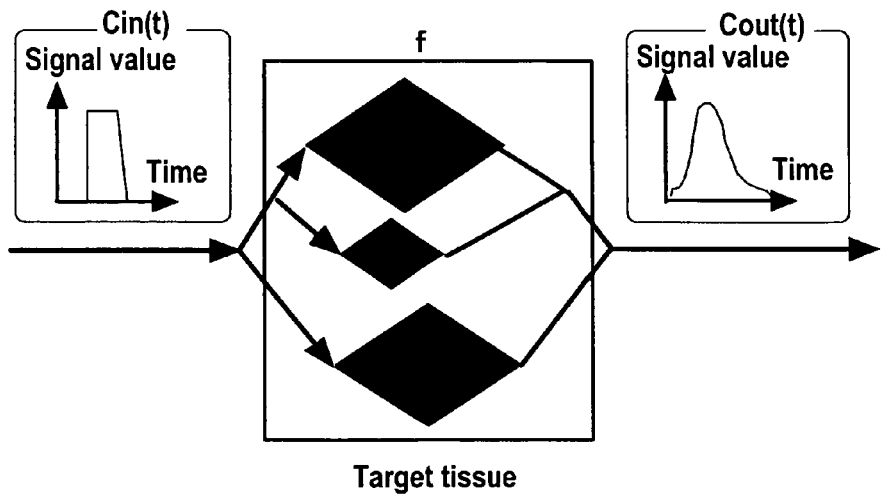
FIG. 7 is a conceptual drawing illustrating an inverse filter method according to the present embodiment.

FIG. 7 is a conceptual drawing illustrating an inverse filter method according to the present embodiment. For a target tissue for a transfer function f, when an input function is defined as Cin(t) and an output function is defined as Cout(t), Cout(t) is obtained by subjecting Cin(t) and f to a convolution integral. This is expressed as follows.

$$Cout(t) = \int_0^t Cin(t) \cdot f(t - t')dt' \tag{4}$$

If a contrast medium is injected into the body through the artery, Cin(t) is replaced with the time-concentration curve (artery input function) AIF(t) for the inflow artery and Cout(t) is replaced with the time-concentration curve Cr(t) for the tissue. This is expressed as follows.

$$Cr(t) = \int_0^t AIF(t) \cdot f(t - t')dt' \tag{5}$$

When Formula (5) is converted into a frequency space, the following formula is given.

$$F\{Cr(t)\} = F\{AIF(t)\} \cdot F\{f(t)\} \tag{6}$$

In this formula, $F\{AIF(t)\}$ denotes a Fourier transformation of AIF(t), $F\{Cr(t)\}$ denotes a Fourier transformation of Cr(t), and $F\{f(t)\}$ denotes a Fourier transformation of f(t).

According to Formulae (5) and (6), the transfer function f can be generated by executing a reverse convolution on the time-concentration curve for the inflow artery and the time-concentration curve for the tissue. However, equivalent calculation results are obtained by multiplying the time-concentration curve for the tissue by the inverse filter of the time-concentration curve for the inflow artery instead of executing a reverse convolution.

When the inverse filter of AIF(t) is defined as $AIF^{-1}(t)$, f(t) is expressed as shown below, on the basis of Formula (6).

$$f(t) = F^{-1}[F\{AIF^{-1}(t)\} \cdot F\{Cr(t)\}] \tag{7}$$

In this formula, $F^{-1}$ denotes a reverse Fourier transformation.

Figure 8:
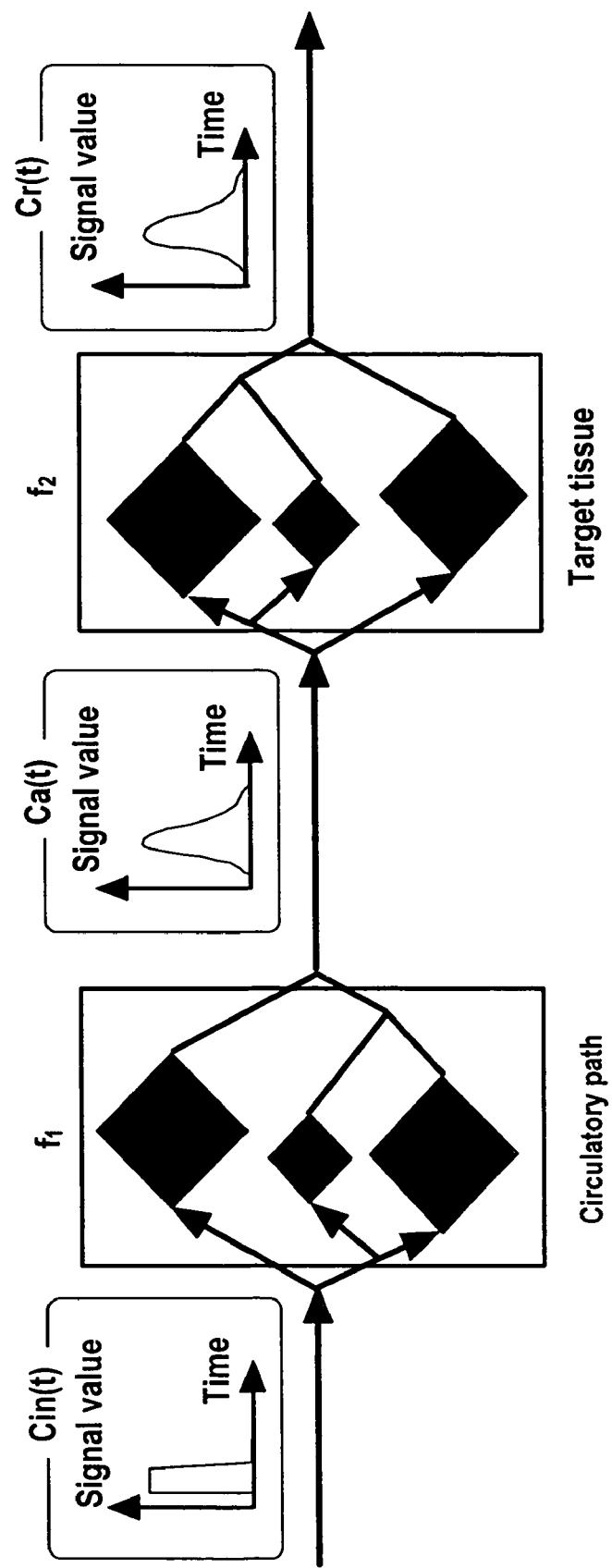
FIG. 8 is a conceptual drawing illustrating the inverse filter method according to the present embodiment.

FIG. 8 is a conceptual drawing illustrating the inverse filter method according to the present embodiment.

For blood flow dynamic analysis, in most cases, the contrast medium is injected into the body through the vein in order to avoid invading the subject. In this case, the contrast medium circulates through the body and then flows into the tissue to be analyzed. The input function is defined as Cin(t). A transfer function for a circulatory path is defined as $f_1$. A transfer function for the target tissue is defined as $f_2$. The output function for the target tissue is defined as Cout(t). Then, Cout(t) is obtained by subjecting Cin(t) and $f_1$ to a convolution integral and subjecting the result and $f_2$ to a convolution integral. Thus, the following formula is given.

$$Cout(t) = \int_0^t \left\{ \int Cin(t) \cdot f_1(t - t'_1) dt'_1 \right\} \cdot f_2(t - t'_2) dt'_2 \tag{8}$$

The convolution integral of Cin(t) and $f_1$ is replaced with the time-concentration curve (artery input function) AIF(t) for the inflow artery. Cout(t) is replaced with the time-concentration curve Cr(t) for the tissue. Thus, the following formula is given.

$$Cr(t) = \int_0^t AIF(t) \cdot f_2(t - t_2') dt_2' \quad (9)$$

Formula (9) is equivalent to Formula (5), previously described. Accordingly, the transfer function $f_2$ is expressed as follows.

$$f_2(t) = F^{-1}[F\{AIF^{-1}(t)\} \cdot F\{Cr(t)\}] \quad (10)$$

Figure 9:
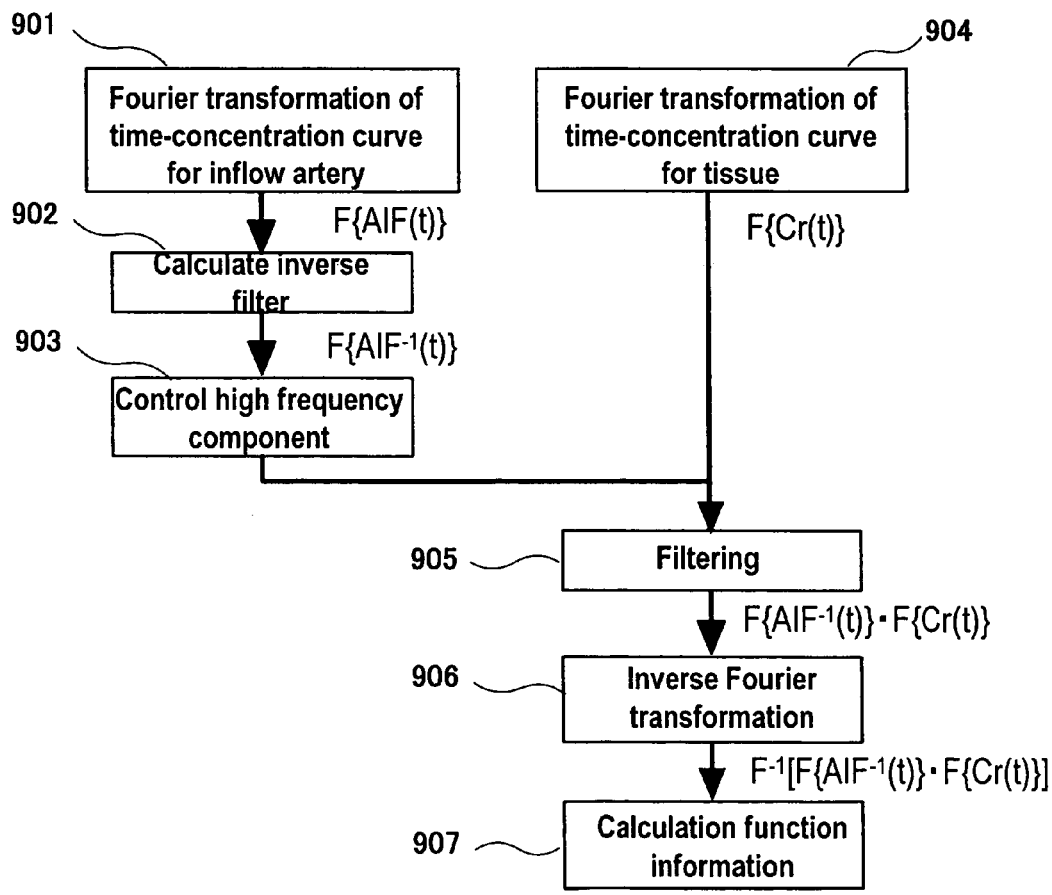
FIG. 9 is a flowchart showing a process procedure of an inverse filter calculation according to the present embodiment.

FIG. 9 is a flowchart showing a process procedure of an inverse filter calculation according to the present embodiment. As shown in FIG. 9, the CPU 5 executes a Fourier transformation on the time-concentration curve for the inflow artery (step 901). Then, the CPU 5 calculates an inverse filter from the Fourier-transformed time-concentration curve for the inflow artery (step 902). When the real part of the Fourier-transformed time-concentration curve for the inflow artery is defined as $F\{AIF_R\}$ and its imaginary part is defined as $F\{AIF_I\}$, the inverse filter is expressed as follows.

$$F\{AIF^{-1}(t)\} = \frac{1}{[F\{AIF_R\} + i\{AIF_I\}]} \quad (11)$$
$$= \frac{F\{AIF_R\}}{[F\{AIF_R\}^2 + \{AIF_I\}^2]} - \frac{iF\{AIF_I\}}{[F\{AIF_R\}^2 + \{AIF_I\}^2]}$$

Then, high-frequency components of the inverse filter are controlled (step 903). The high-frequency components of the inverse filter are controlled by filtering the inverse filter using a high-frequency control filter such as a Wiener filter or a Butterworth filter. Subsequently, the CPU 5 executes a Fourier transformation on the time-concentration curve for each tissue (step 904). The CPU 5 uses the inverse filter determined in step 902 to filter the Fourier-transformed time-concentration curve for the tissue (step 905). The CPU 5 thus generates a transfer function that executes an inverse Fourier transformation on the filtered Fourier-transformed time-concentration curve for the tissue (step 906).

Then, the CPU 5 calculates biological function information such as the blood flow dynamics from the transfer function determined in step 906 (step 907). A method for calculating biological function information will be described below. Steps 904 to 907 are repeated a number of times equal to the number of pixels on the tomogram of the tissue to be analyzed. Additionally, it is possible to reverse the processing from step 901 to step 903 and the processing in step 904.

Now, description will be given of a method for calculating biological function information from the transfer function.

Figure 10:
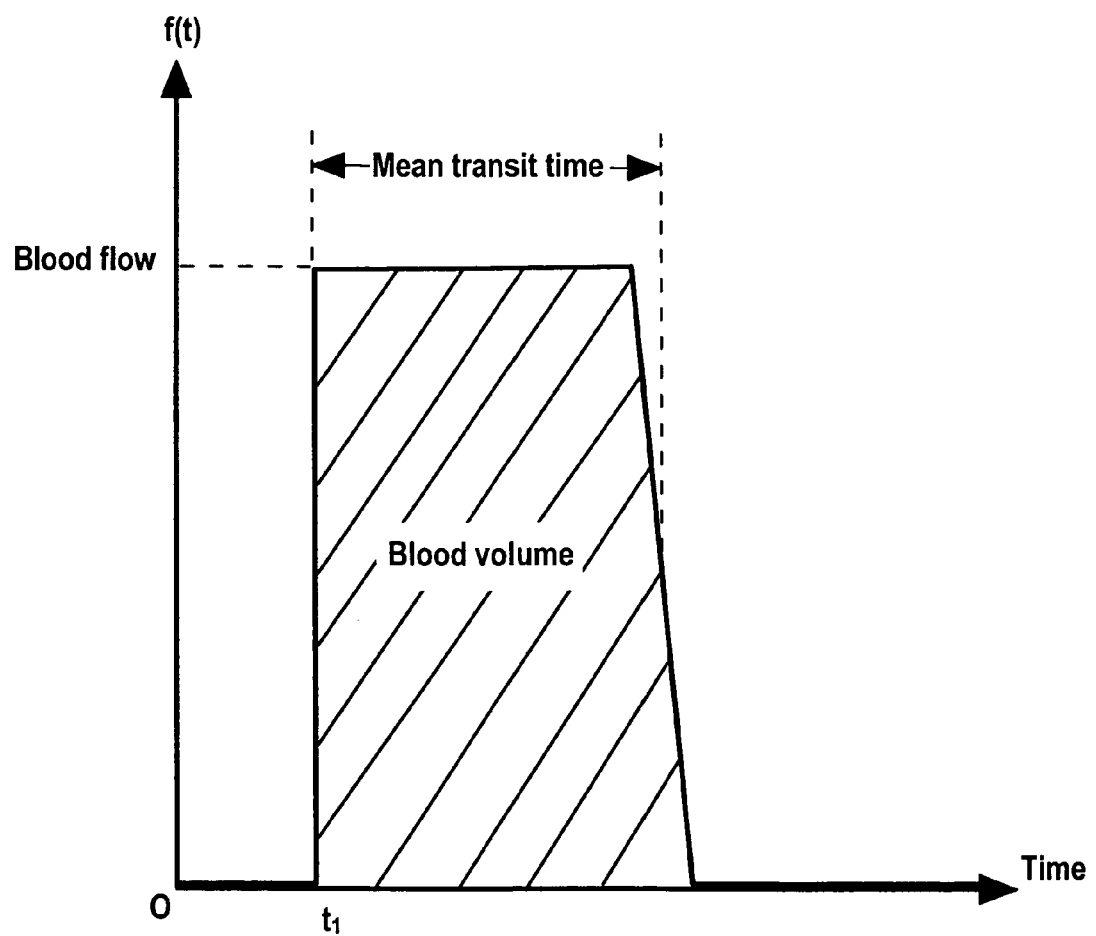
FIG. 10 is a diagram illustrating a method for calculating biological function information.

FIG. 10 is a diagram illustrating a method for calculating biological function information. When the transfer function is defined as f(t), f(t) has, for example, such a shape as shown in FIG. 10. The blood flow (referred to as "BF" below) is determined from the maximum value of f(t) as shown below.

$$BF = f_{max} \quad (12)$$

Further, the blood volume (referred to as BV below) is determined from the area under the curve of f(t) as shown below.

$$BV = \int f(t) dt \quad (13)$$

The mean transit time (referred to as MIT below) is determined from the width of f(t) as shown below.

$$MTT = \int \frac{f(t)dt}{f_{max}} \quad (14)$$

In this formula, $f_{max}$ denotes the maximum value of f(t).

Now, description will be given of a method for determining a high-frequency control filter. In order to calculate a transfer function in accordance with Formula (9), it is necessary to execute an inverse convolution on the time-concentration curve for the artery and the time-concentration curve for the tissue. The inverse convolutions are roughly classified into methods such as singular value decomposition method which use a determinant and methods such as the inverse filtering method which uses a Fourier transformation. The method using a Fourier transformation can reduce the time required for calculations compared to the method using a determinant. With the inverse filtering method, the Fourier-transformed time-concentration curve for the tissue is filtered on a frequency space using the inverse filter calculated from the Fourier-transformed time-concentration curve for the artery. This calculation is a process for emphasizing the high frequency components. In general, biological signal components appear in a low frequency region, while noise components appear in a high frequency region. Accordingly, simple inverse filtering calculations unnecessarily emphasizes noise, making it difficult to accurately obtain biological function information. Thus, the high frequency components must be controlled for the inverse filter.

Figure 11A:
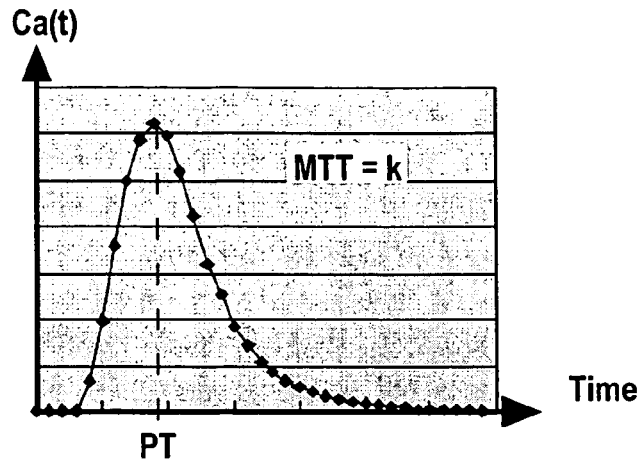
FIGS. 11(a) to 11(c) are diagrams illustrating a method 1 for calculating a high-frequency control filter.

It is assumed that the artery input function for the target tissue, that is, the time-concentration curve for the inflow artery, has been actually measured as shown in FIG. 11a. The mean transit time ($MTT_{Artery}$) of this time-concentration curve is determined as follows.

$$MTT_{Artery} = \frac{\sum_{t=0}^{n} t \cdot Ca(t)}{\sum_{t=0}^{n} Ca(t)} \quad (15)$$

Figure 11B:
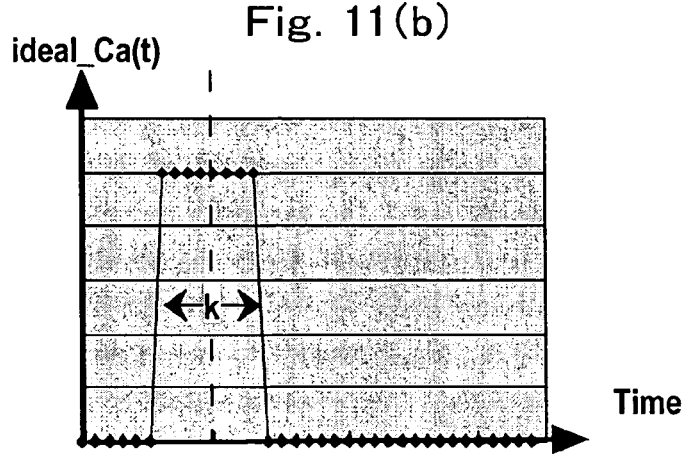
Figure 11C:
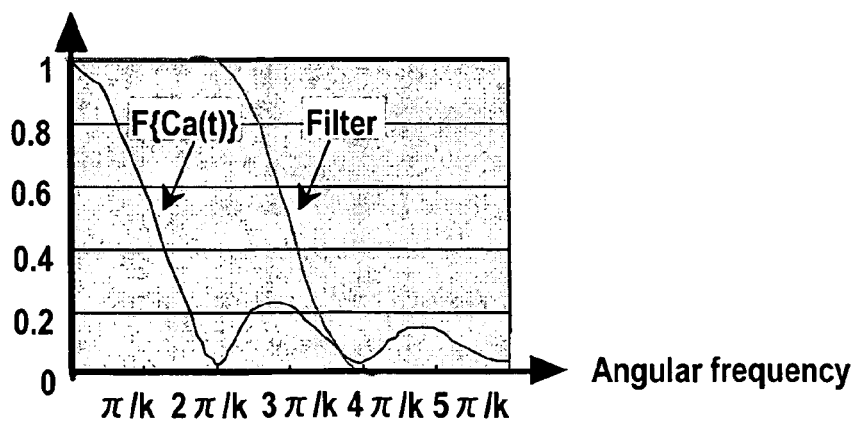

In this formula, t denotes a time, n denotes the number of measuring points, and Ca(t) denotes a time-concentration curve. Such an ideally rectangular input function ideal_Ca(t) as shown in FIG. 11(b) is determined from the peak time (PT in FIG. 11) of the time-concentration curve for the inflow artery and the mean transit time determined using Formula (16); the width of the ideally rectangular input function around the peak time is equal to the mean transit time. When Fourier-transformed ideal_Ca(t) is defined as F{ideal_Ca(t)}, F{ideal_Ca(t)} is as shown in FIG. 11(c). In this case, useful ecological information appears as low frequency components, while noise components that are insignificant for the analysis appear as high frequency components. Accordingly, for F{ideal_Ca(t)}, for example, as shown in FIG. 11(c), only the components from the angular frequency 0 to (2π)/k are left as they are, components from (2π)/k to (4π)/k are attenuated, and frequency components exceeding (4π)/k are cut for determining a shape of the filter. This high frequency control filter is given by the following formula.

$$\text{filter}(\omega) = \begin{cases} 1 & 0 \leq \omega \leq \omega_s \\ \frac{1}{2} + \cos\left\{\frac{\pi}{2(\omega_e - \omega_s)}(\omega - \omega_s)\right\} & \omega_s \leq \omega \leq \omega_e \\ 0 & \omega_e \leq \omega \end{cases} \quad (16)$$

Figure 12:
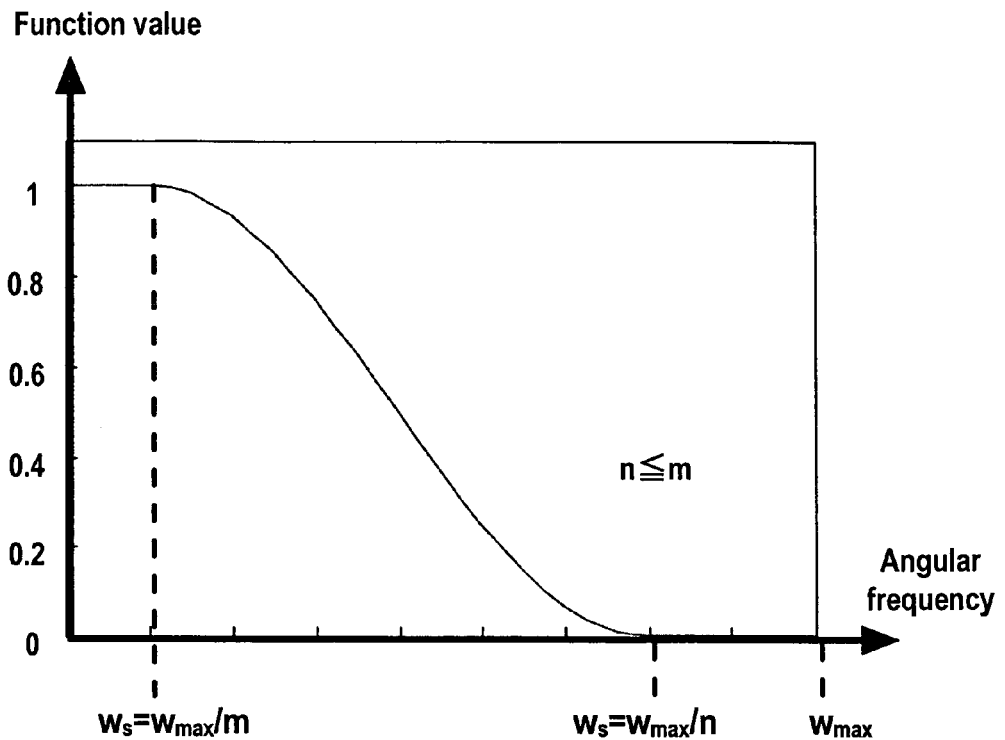
FIG. 12 is a diagram illustrating a method 2 for calculating a high-frequency control filter.

In this formula, ω denotes an angular frequency, ωs denotes a control start frequency, and ωe denotes a control end frequency. When the width of ideal _Ca(t), that is, the mean transit time of Ca(t) is defined as k, ωs=(2π)/k and ωe=(4π)/k. Accordingly, the shape of the high-frequency region control filter is determined from the time-concentration curve for the inflow artery. In the description of the present embodiment, for convenience, ωs=(2π)/k and ωe=(4π)/k. However, ωs and ωe are not limited to this. Arbitrary settings are possible; ωs=(nπ)/k and ωe=(2π)/k (m≦n). In the present embodiment, ωs and ωe are calculated from the time-concentration curve for the inflow artery. However, the method for calculating ωs and ωe is not limited to this. An arbitrary setting is possible using the maximum frequency as shown in FIG. 12.

The high frequency control filter may be as shown below.

$$\begin{bmatrix} \text{filter}(\omega) = \text{filter2}(\omega) + k\{\text{filter2}(\omega) - \text{filter1}(\omega)\} & (17) \\ \text{filter1}(\omega) = \begin{cases} 1 & 0 \leq \omega \leq \omega 1_s \\ \frac{1}{2} + \cos\left\{\frac{\pi}{2(\omega 1_e - \omega 1_s)}(\omega - \omega 1_s)\right\} & \omega 1_s \leq \omega \leq \omega 1_e \\ 0 & \omega 1_e \leq \omega \end{cases} \\ \text{filter2}(\omega) = \begin{cases} 1 & 0 \leq \omega \leq \omega 2_s \\ \frac{1}{2} + \cos\left\{\frac{\pi}{2(\omega 2_e - \omega 2_s)}(\omega - \omega 2_s)\right\} & \omega 2_s \leq \omega \leq \omega 2_e \\ 0 & \omega 2_e \leq \omega \end{cases} \end{bmatrix}$$

Figure 13:
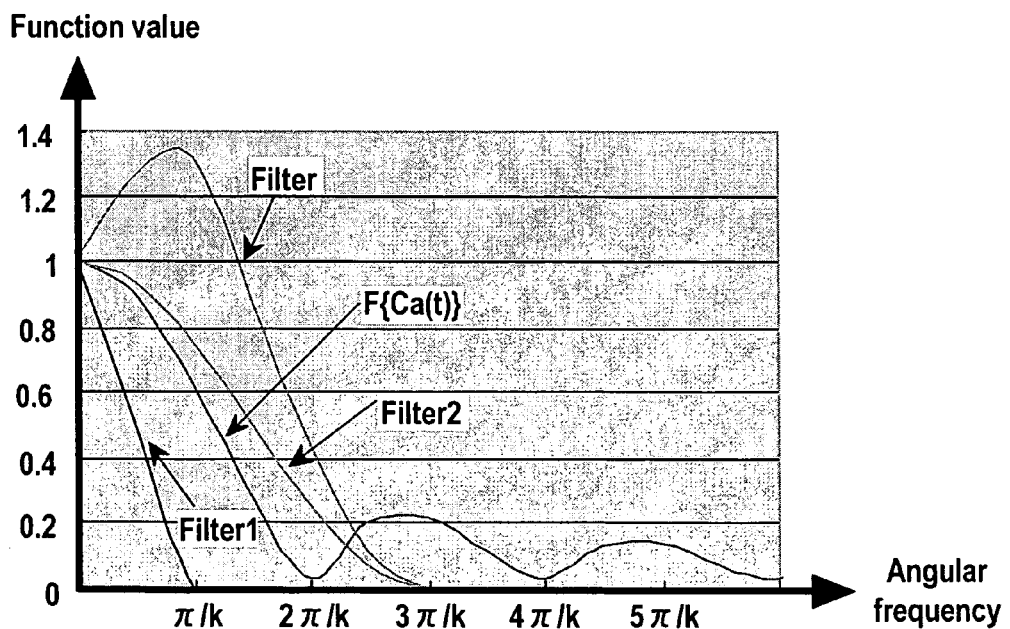
FIG. 13 is a diagram illustrating a method 3 for calculating a high-frequency control filter.

The filter expressed by Formula (17) suppresses the high frequency components while emphasizing the low frequency components. In this formula, k denotes a parameter indicating how the low frequency components are emphasized. If the following settings are made: ω1s=0, ω1e=π/k, ω2s=0, ω2e=(3π)/k, and k=0.75, such a high-frequency control filter as shown in FIG. 13 is obtained. In the present embodiment, ω1s, ω1e, ω2s, and ω2e are calculated from the time-concentration curve for the inflow artery. However, the calculating method is not limited to this. These values may be arbitrarily set on the basis of the maximum frequency.

Further, the high-frequency control filter may display a graph showing the progress of measurements on an image display section provided in a computer tomogram diagnosing apparatus. In connection with this graph, it is possible to allow at least one of various parameters provided for the high-frequency control filter to be varied by using a well-known graphical user interface that uses a pointing device such as a mouse or a track ball to, for example, vary the shape of the displayed graph. The various parameters include the control frequency of the high-frequency control filter and the degree of the emphasis of the low frequency area.

Thus, the original signal can be appropriately emphasized by varying the various parameters, for example, increasing the control frequency band of the high-frequency control filter or the degree of the emphasis of the low-frequency area. As a result, the number of signal components increases to suppress the noise components. An optimum high-frequency control filter can thus be provided. This makes it possible to provide an image subjected to high-definition biological function information analysis for blood flow dynamics.

As described above, according to the above embodiment, if biological function information analysis is to be executed on a tomogram dynamically acquired using a computer tomogram diagnosing apparatus, the analysis can be accomplished with a contrast rate lower than that of the first moment method (gamma-fitting method) or maximum slope method and with a calculation time shorter than that of the deconvolution method. The embodiment is also effective in preventing the degradation of quantitativeness attributed to the PVA effect. The embodiment is also effective in preventing an unnecessary increase in calculation time owing to unwanted areas and analysis precision without increasing a burden on the operator.

What is claimed is:

1. A blood flow dynamic analyzing apparatus, comprising:
an input means which inputs a tomogram acquired by tomogram imaging means;
a first calculating means which determines a time-concentration curve indicative of information on a temporal variation in each pixel of the tomogram input by the input means;
a second calculating means which determines a time-concentration curve for an inflow artery from the time-concentration curve for each pixel of the tomogram determined by the first calculating means;
a third calculating means which generates an inverse filtering function from the time-concentration curve for the inflow artery extracted by the second calculating means;
a fourth calculating means which generates a transfer function for each pixel of the tomogram on the basis of the reverse filtering function generated by the third calculating means and the time-concentration curve for each pixel of the tomogram determined by the first calculating means; and
a fifth calculating means which forms a blood flow dynamic analysis image by using the transfer function for each pixel of the tomogram generated by the fourth calculating means.

2. The blood flow dynamic analyzing apparatus according to claim 1, wherein the third calculating means comprises a high-frequency control filtering means which controls high frequency components of the inverse filtering function generated.

3. The blood flow dynamic analyzing apparatus according to claim 2, wherein the high-frequency control filter means comprises a filtering function calculating means which generates a filtering function on the basis of the time-concentration curve for the inflow artery extracted by the second calculating means.

4. The blood flow dynamic analyzing apparatus according to claim 3, wherein the filtering function calculating means executes a Fourier transformation on the time-concentration curve for the inflow artery extracted by the second calculating means, sets a control start frequency and a control end frequency for the high-frequency control filtering means on the basis of the Fourier-transformed time-concentration curve for the inflow artery, and generates a filtering function for the high-frequency control filtering means on the basis of the set control start frequency and control end frequency.

5. The blood flow dynamic analyzing apparatus according to claim 4, wherein the control start frequency and the control end frequency are determined on the basis of a maximum frequency of the Fourier-transformed time-concentration curve for the inflow artery.

6. The blood flow dynamic analyzing apparatus according to claim 2, wherein the high-frequency control filtering means comprises a parameter setting means which sets at least one parameter of a degree to which a low frequency part of the high-frequency control filter is emphasized and a band of the high-frequency control filter.

7. The blood flow dynamic analyzing apparatus according to claim 6, wherein the parameter setting means comprises a display means which displays the filtering function of the high-frequency control filtering means and a varying means which varies the filtering function displayed by the display means.

8. The blood flow dynamic analyzing apparatus according to claim 7, wherein the varying means varies a shape of the high-frequency control filtering function displayed on the display means using a graphic user interface.

9. The blood flow dynamic analyzing apparatus according to claim 1, further comprising:
an extracting means which extracts a maximum connected pixel area in the tomogram input by the input means; and
a removing means which removes areas unnecessary for blood flow dynamic analysis from the tomogram input by the input means on the basis of the maximum connected pixel area extracted by the extracting means.

10. The blood flow dynamic analyzing apparatus according to claim 9, wherein the unnecessary areas include room air, a bed, and bones.

11. The blood flow dynamic analyzing apparatus according to claim 1, further comprising:
a determining means which determines a time-concentration curve for an outflow vein from the time-concentration curve for each pixel of the tomogram input by the input means and finding peak values of the determined time-concentration curve for the inflow artery and the determined time-concentration curve for the outflow vein; and
a correcting means which corrects a partial volume averaging effect on the time-concentration curve for the inflow artery so that the found peak value of the time-concentration curve for the inflow artery matches the found peak value of the time-concentration curve for the outflow vein.

12. A blood flow dynamic analyzing method, comprising:
an input step of inputting a tomogram acquired by a tomogram imaging apparatus;
a first calculating step of determining a time-concentration curve indicative of information on a temporal variation in each pixel of the tomogram input by the input step;
a second calculating step of determining a time-concentration curve for an inflow artery from the time-concentration curve for each pixel of the tomogram determined by the first calculating step;
a third calculating step of generating an inverse filtering function from the time-concentration curve for the inflow artery extracted by the second calculating step;
a fourth calculating step of generating a transfer function for each pixel of the tomogram on the basis of the reverse function generated by the third calculating step and the time-concentration curve for each pixel of the tomogram determined by the first calculating step; and
a fifth calculating step of forming a blood flow dynamic analysis image by using the transfer function for each pixel of the tomogram generated by the fourth calculating step.

13. The blood flow dynamic analyzing method according to claim 12, wherein the third calculating step comprises a high-frequency control filtering step of controlling high frequency components of the inverse filtering function generated.

14. The blood flow dynamic analyzing method according to claim 13, wherein the high-frequency control filter step comprises a filtering function calculating step of generating a filtering function on the basis of the time-concentration curve for the inflow artery extracted in the second calculating step.

15. The blood flow dynamic analyzing method according to claim 14, wherein the filtering function calculating step executes a Fourier transformation on the time-concentration curve for the inflow artery extracted in the second calculating step, sets a control start frequency and a control end frequency for the high-frequency control filtering means on the basis of the Fourier-transformed time-concentration curve for the inflow artery, and generates a filtering function for the high-frequency control filtering means on the basis of the set control start frequency and control end frequency.

16. The blood flow dynamic analyzing method according to claim 15, wherein the control start frequency and the control end frequency are determined on the basis of a maximum frequency of the Fourier-transformed time-concentration curve for the inflow artery.

17. The blood flow dynamic analyzing method according to claim 13, wherein the high-frequency control filtering step comprises a parameter setting step of setting at least one parameter of a degree to which a low frequency part of the high-frequency control filter is emphasized and a band of the high-frequency control filter.

18. The blood flow dynamic analyzing method according to claim 17, wherein the parameter setting step comprises:
a display step of displaying the filtering function of the high-frequency control filtering means on a display unit; and
a step of varying the filtering function displayed in the display step.

19. The blood flow dynamic analyzing method according to claim 18, wherein the varying step varies a shape of the high-frequency control filtering function displayed in the display step using a graphic user interface.

20. The blood flow dynamic analyzing method according to claim 12, further comprising:
an extracting step of extracting a maximum connected pixel area in the tomogram input in the input step; and
a step of removing areas unnecessary for blood flow dynamic analysis from the tomogram input in the input step on the basis of the maximum connected pixel area extracted in the extracting step.

21. The blood flow dynamic analyzing method according to claim 20, wherein the unnecessary areas include room air, a bed, and bones.

22. The blood flow dynamic analyzing method according to claim 12, further comprising:
a step of determining a time-concentration curve for an outflow vein from the time-concentration curve for each pixel of the tomogram input by the input means and finding peak values of the determined time-concentration curve for the inflow artery and the determined time-concentration curve for the outflow vein; and
a correcting step of correcting a partial volume averaging effect on the time-concentration curve for the inflow artery so that the found peak value of the time-concentration curve for the inflow artery matches the found peak value of the time-concentration curve for the outflow vein.

23. An image diagnosing apparatus that can acquire a tomogram of a living body, comprising:

an input means which inputs a tomogram acquired by tomogram imaging means;

a first calculating means which determines a time-concentration curve indicative of information on a temporal variation in each pixel of the tomogram input by the input means;

a second calculating means which determines a time-concentration curve for an inflow artery from the time-concentration curve for each pixel of the tomogram determined by the first calculating means;

a third calculating means which generates an inverse filtering function from the time-concentration curve for the inflow artery extracted by the second calculating means;

a fourth calculating means which generates a transfer function for each pixel of the tomogram on the basis of the reverse filtering function generated by the third calculating means and the time-concentration curve for each pixel of the tomogram determined by the first calculating means; and a fifth calculating means which forms a blood flow dynamic analysis image by using the transfer function for each pixel of the tomogram generated by the fourth calculating means.

24. The image diagnosing apparatus according to claim 23, wherein the third calculating means comprises a high-frequency control filtering means which controls high frequency components of the inverse filtering function generated.

25. The image diagnosing apparatus according to claim 24, wherein the high-frequency control filtering means comprises a filtering function calculating means for generating a filtering function on the basis of the time-concentration curve for the inflow artery extracted by the second calculating means.

26. The image diagnosing apparatus according to claim 25, wherein the filtering function calculating means executes a Fourier transformation on the time-concentration curve for the inflow artery extracted by the second calculating means, sets a control start frequency and a control end frequency for the high-frequency control filtering means on the basis of the Fourier-transformed time-concentration curve for the inflow artery, and generates a filtering function for the high-frequency control filtering means on the basis of the set control start frequency and control end frequency.

27. The image diagnosing apparatus according to claim 26, wherein the control start frequency and the control end frequency are determined on the basis of a maximum frequency of the Fourier-transformed time-concentration curve for the inflow artery.

28. The image diagnosing apparatus according to claim 24, wherein the high-frequency control filtering means comprises a parameter setting means which sets at least one parameter of a degree to which a low frequency part of the high-frequency control filter is emphasized and a band of the high-frequency control filter.

29. The image diagnosing apparatus according to claim 28, wherein the parameter setting means comprises a display means which displays the filtering function of the high-frequency control filtering means and a varying means which varies the filtering function displayed by the display means.

30. The image diagnosing apparatus according to claim 29, wherein the varying means varies a shape of the high-frequency control filtering function displayed on the display means using a graphic user interface.

* * * * *